US011001452B2

(12) United States Patent
Shaw et al.

(10) Patent No.: US 11,001,452 B2
(45) Date of Patent: May 11, 2021

(54) CONVEYOR APPARATUS FOR IMAGING FOOD PRODUCTS

(71) Applicant: P & P OPTICA INC., Waterloo (CA)

(72) Inventors: Anthony Robert Shaw, Waterloo (CA); Alexander Baran-Harper, Waterloo (CA); Hernan Miguel Hinojosa, Waterloo (CA); Timothy M. F. Stork, Kitchener (CA)

(73) Assignee: P & P OPTICA INC., Waterloo (CA)

( * ) Notice: Subject to any disclaimer, the term of this patent is extended or adjusted under 35 U.S.C. 154(b) by 0 days.

(21) Appl. No.: 15/998,438

(22) Filed: Aug. 15, 2018

(65) Prior Publication Data

US 2020/0055678 A1    Feb. 20, 2020

(51) Int. Cl.
*B65G 47/24* (2006.01)
*G01N 21/27* (2006.01)
*G01N 33/02* (2006.01)

(52) U.S. Cl.
CPC ............. *B65G 47/24* (2013.01); *G01N 21/27* (2013.01); *G01N 33/02* (2013.01)

(58) Field of Classification Search
CPC ......... B65G 47/24; G01N 21/27; G01N 33/02
See application file for complete search history.

(56) References Cited

U.S. PATENT DOCUMENTS

| 5,141,097 | A | 8/1992 | Oiry et al. |
| 6,471,044 | B1 | 10/2002 | Isaacs et al. |
| 6,609,607 | B2 * | 8/2003 | Woltjer ................ B65G 37/02 198/457.03 |
| 6,646,218 | B1 * | 11/2003 | Campbell ............... A24B 1/04 209/577 |
| 6,955,255 | B2 * | 10/2005 | Dickinson .............. B65G 15/14 198/603 |

(Continued)

FOREIGN PATENT DOCUMENTS

| WO | WO-0183340 A1 | 11/2001 |
| WO | WO-2017167446 A1 | 10/2017 |

OTHER PUBLICATIONS

ISA/CA, International Search Report and Written Opinion, dated Jan. 9, 2020, re PCT International Patent Application No. PCT/IB2019/056911.

(Continued)

*Primary Examiner* — Violeta A Prieto
(74) *Attorney, Agent, or Firm* — Perry + Currier, Inc.

(57) ABSTRACT

Apparatuses for imaging food products are provided. An apparatus includes a first and second conveyor, the first conveyor configured to move a flexible food product at a first speed, the second conveyor configured to move the flexible food product at a second speed greater than the first speed, a receiving portion of the second conveyor positioned in a downward direction relative to the first conveyor to receive the flexible food product, thereby flipping the flexible food product and stretching the flexible food product for imaging. An apparatus may include a guide mechanism to guide the food product to be flipped. An apparatus may move a plurality of food products and spread apart the plurality of food products for imaging. An apparatus may include a receiving structure having a low-friction receiving surface for stretching or spreading apart food products.

17 Claims, 12 Drawing Sheets

(56) References Cited

U.S. PATENT DOCUMENTS

| | | | | |
|---|---|---|---|---|
| 2001/0030102 A1* | 10/2001 | Woltjer | ............... | B65G 37/02 |
| | | | | 198/388 |
| 2005/0077150 A1* | 4/2005 | Dickinson | ............. | B65G 15/14 |
| | | | | 198/603 |
| 2005/0279614 A1* | 12/2005 | Dickinson | ............. | B65G 15/14 |
| | | | | 198/603 |
| 2010/0040442 A1* | 2/2010 | Jorgensen | ......... | B65G 21/2054 |
| | | | | 414/222.07 |
| 2014/0147015 A1* | 5/2014 | Bajema | ............... | G06T 7/0004 |
| | | | | 382/110 |
| 2015/0158676 A1* | 6/2015 | Finnsson | ............... | B65G 21/14 |
| | | | | 198/444 |

OTHER PUBLICATIONS

PCT/IB2019/056911, Conveyor Apparatus for Imaging Food Products, Aug. 14, 2019.

\* cited by examiner

CONVEYOR APPARATUS FOR IMAGING FOOD PRODUCTS

BACKGROUND

Imaging of food products to determine quality, and the like, can be challenging. In some approaches, imaging devices acquire images of food products being conveyed (e.g. in a factory) using a conveyor. However, the food products may be positioned or oriented on a conveyor in such a way that hinders or obstructs imaging devices from capturing image data from portions of the food products.

BRIEF DESCRIPTION OF THE DRAWINGS

For a better understanding of the various embodiments described herein and to show more clearly how they may be carried into effect, reference will now be made, by way of example only, to the accompanying drawings in which.

DETAILED DESCRIPTION

Figure 1:
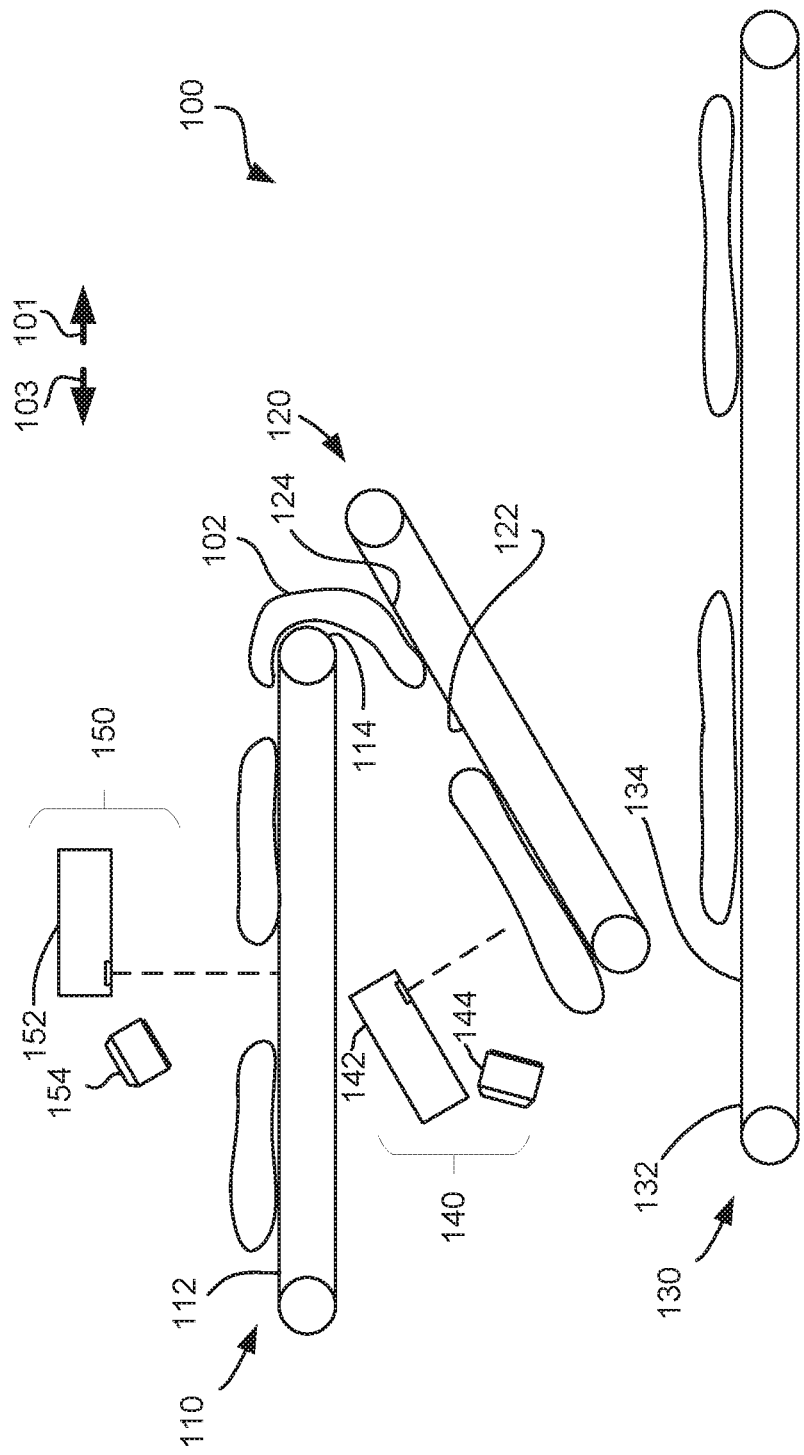
FIG. 1 depicts a schematic view of an apparatus for imaging food products with conveyors configured in a z-configuration, according to non-limiting examples.

Food products may be analyzed for quality and other characteristics (e.g. in a factory) by conveying food products down a conveyor, capturing images of the food products as they are conveyed down the conveyor, and analyzing the captured image data. In this way, quality and other characteristics of meats, vegetables, fruits, nuts, and other food products may be determined.

However, the food products to be analyzed may be positioned or oriented on a conveyor in such a way that hinders or obstructs imaging devices from capturing image data from portions of the food products which are obscured or otherwise concealed from view of the imaging devices. For example, some food products, such as chicken breasts and other irregularly shaped meats, may include folds or creases which obscure portions of the surface area of the food product from the view of imaging devices. As another example, some food products, such as steaks and other meat products, may include crevices in which foreign objects and other undesirable contaminants, organic or inorganic, may reside, concealed from the view of imaging devices. Conveyors may be configured to manipulate such food products, for example by stretching or spread the food products, so that the concealment caused by folds, creases, and crevices, and the like, may be reduced, thereby allowing the food products to be analyzed with greater accuracy. In addition, guiding mechanisms may be used to assist with the stretching, spreading, flipping, or otherwise manipulating the food products.

Furthermore, large groups of numerous food products may bunch, clump, or group up on a conveyor, which similarly may lead to the obstruction of certain portions of the food products from view. For example, a leafy vegetable such as spinach may overlap with other spinach leaves, and irregularly shaped fruits, nuts, or beans may be positioned in such a way that a portion of one food product may obscure a portion of another. Thus, a plurality of food products may be analyzed with greater accuracy if the food products were to be spread apart on the conveyor to allow for greater spacing between individual food products. Additionally, spreading apart dense groups of food product may relieve the burden on imaging devices and analytical systems to image and analyze large quantities of food product in a short period of time.

An apparatus includes a first conveyor having a first conveying surface and a terminal end, the first conveyor configured to move a flexible food product at a first speed on the first conveying surface off the terminal end of the first conveyor. The apparatus includes a second conveyor having a second conveying surface and a receiving portion, the second conveying surface at the receiving portion positioned in a downward direction relative to the terminal end of the first conveyor to receive the flexible food product moved off the terminal end of the first conveyor, thereby flipping the flexible food product, the second conveyor configured to move the flexible food product at a second speed greater than the first speed to stretch the flexible food product as it is received by the second conveying surface. The apparatus includes a first imaging device oriented to capture a first image of the flexible food product on the second conveying surface.

Another apparatus includes a first conveyor having a first conveying surface and a terminal end, the first conveyor configured to move a food product at a first speed on the first conveying surface off the terminal end, the food product comprising a first side and a second side opposite the first side, the first side facing away from the first conveying surface when the food product is on the first conveying surface. The apparatus includes a first imaging device oriented to capture a first image of the food product on the first conveying surface. The apparatus includes a second conveyor having a second conveying surface and a receiving portion, the second conveying surface at the receiving portion positioned in a downward direction relative to the terminal end of the first conveyor to receive the food product moved off the terminal end of the first conveyor. The apparatus includes a guide mechanism to guide the food product to be flipped onto its first side to be received onto the second conveying surface. The apparatus includes a second imaging device oriented to capture a second image of the food product on the second conveying surface.

Another apparatus includes a first conveyor having a first conveying surface and a terminal end, the first conveyor configured to move a plurality of food products at a first speed on the first conveying surface off the terminal end. The apparatus includes a second conveyor having a second conveying surface to receive the plurality of food products moved off the terminal end of the first conveyor, the second conveyor configured to move the plurality of food products at a second speed greater than the first speed to spread apart the plurality of food products. The apparatus includes a first imaging device oriented to capture a first image of the plurality of food products on the second conveying surface.

Another apparatus includes a conveyor and a receiving structure below the conveyor, with the receiving structure having a low-friction receiving surface to move a food product at a greater speed along the receiving structure than along the first conveyor, thereby stretching, spreading, or spreading apart the food product.

Another apparatus may include a guide mechanism such an air jet, air knife, roller, or deflecting sheet, to assist with flipping food products. In some examples, the apparatus may include a first conveyor and a second conveyor, wherein the second conveyor moves the food products at a speed greater than or equal to the speed at which the first conveyor moves the food products (e.g. including where the second conveyor moves the food products at the same speed as the first conveyor), wherein a guide mechanism guides the transfer of the food products from the first conveyor to the second conveyor.

FIG. 1 depicts a schematic view of an apparatus 100 for imaging food products, according to non-limiting examples. The apparatus 100 may be used for imaging flexible and/or stretchable and/or spreadable food products. A flexible food product may include any food product which may be stretched or spread to lengthen its surface or to reveal additional surface area, such as meat cuts, slabs, patties, or other flexible foods.

The apparatus 100 includes a first conveyor 110 having a first conveying surface 112 and a terminal end 114. The first conveyor 110 moves flexible food products along the first conveying surface 112 toward the terminal end 114. The flexible food products are moved off the first conveyor 110 at the terminal end 114.

The apparatus 100 includes a second conveyor 120 having a second conveying surface 122 and a receiving area and/or portion 124. The second conveying surface 122 at the receiving portion 124 is positioned in a downward direction relative to the terminal end 114 of the first conveyor 110. In other words, the receiving portion 124 of the second conveyor 120 is below the terminal end 114 of the first conveyor 110. Thus, a flexible food product 102, shown moving off the terminal end 114 of the first conveyor 110, is received onto the second conveyor 120 at the second conveying surface 122.

Further, the first conveyor 110 and second conveyor 120 are configured such that the flexible food product 102 is flipped as it is transferred from the first conveyor 110 to the second conveyor 120. Flipping the flexible food product 102 is achieved, in part, by the first conveyor 110 moving the flexible food product 102 generally in a forward direction 101, and the second conveyor 120 moving the flexible food product 102 generally in a reverse direction 103, opposite to the forward direction 101. Further discussion of manipulating the transfer of the flexible food product 102 from the first conveyor 110 to the second conveyor 120 is provided with reference to FIG. 2, below.

Continuing with reference to FIG. 1, the apparatus 100 further includes a lower imaging device 140. The lower imaging device 140 is oriented to capture images of a flexible food products on the second conveying surface 122, which may be used to analyze the flexible food products, for example to determine quality thereof and/or when contaminants are present. The lower imaging device 140 includes an imager 142, and may include a lighting device 144 to light a flexible food product being imaged. In some examples, the imaging device 140 may include a spectrometer, such as a line-scan spectrometer. In yet further examples, the lower imaging device 140 may comprise a combination of a camera, such as a line-scan camera, and a spectrometer, such as a line-scan spectrometer.

The apparatus 100 may include an upper imaging device 150 oriented to capture images of flexible food products on the first conveying surface 112, which may be used to analyze the flexible food products, for example to determine quality thereof and/or when contaminants are present. Similarly, the upper imaging device 150 includes an imager 152, and may include a lighting device 154 to light a food product being imaged. In some examples, the upper imaging device 150 may include a spectrometer, such as a line-scan spectrometer. In yet further examples, the upper imaging device 150 may comprise a combination of a camera, such as a line-scan camera, and a spectrometer, such as a line-scan spectrometer.

The first conveyor 110 and second conveyor 120 are configured to flip the flexible food product 102 as it is transferred from the first conveyor 110 to the second conveyor 120. Thus, the lower imaging device 140 captures an image of a side of the flexible food products after being flipped, and the upper imaging device 150 may capture an image of the opposite side of the food product prior to flipping.

The first conveyor 110 moves flexible food products at a first speed, and the second conveyor 120 moves flexible food products at a second speed that is greater than the first speed. Thus, as the flexible food product 102 is transferred from the first conveyor 110 to the second conveyor 120, the flexible food product 102 is stretched lengthwise in the forward direction 101. Thus, any folds, creases, or crevices and the like, which may obscure portions of the flexible food products from the view of imaging devices may be revealed to the lower imaging device 140. The imaging device 140 may thereby detect foreign material contaminating the flexible food product 102 that would otherwise have been obscured from view.

Further, stretching the flexible food product 102 may enhance the image data captured by the imaging device 140. After the flexible food product 102 has been stretched, additional surface area may be made available for light to penetrate and interact with more surface area of the flexible food product 102, resulting in a reflected light which contains richer information about the composition and/or quality of the flexible food product 102, which may enable a more accurate analysis of the light reflecting off the flexible food product 102.

The apparatus 100 may include a third conveyor 130 which includes a third conveying surface 132 and receiving portion 134. A portion of the third conveying surface 132 may be positioned in a downward direction relative to the second conveyor 120. In other words, the third conveyor 130 may be below the second conveyor 120. Further, the third conveyor 130 may move flexible food products in the forward direction 101. Thus, the first conveyor 110, second conveyor 120, and third conveyor 130 may together generally take on side profile form resembling the letter "Z", and the conveyors of the apparatus 100 may be described as being configured in a Z-configuration.

Although not shown, it will now be understood that the second conveyor 120 and third conveyor 130 may be configured to flip and stretch flexible food products transferred from the second conveyor 120 to the third conveyor 130, and that another image of the other side thereof may be captured by a further imaging device.

Figure 2:
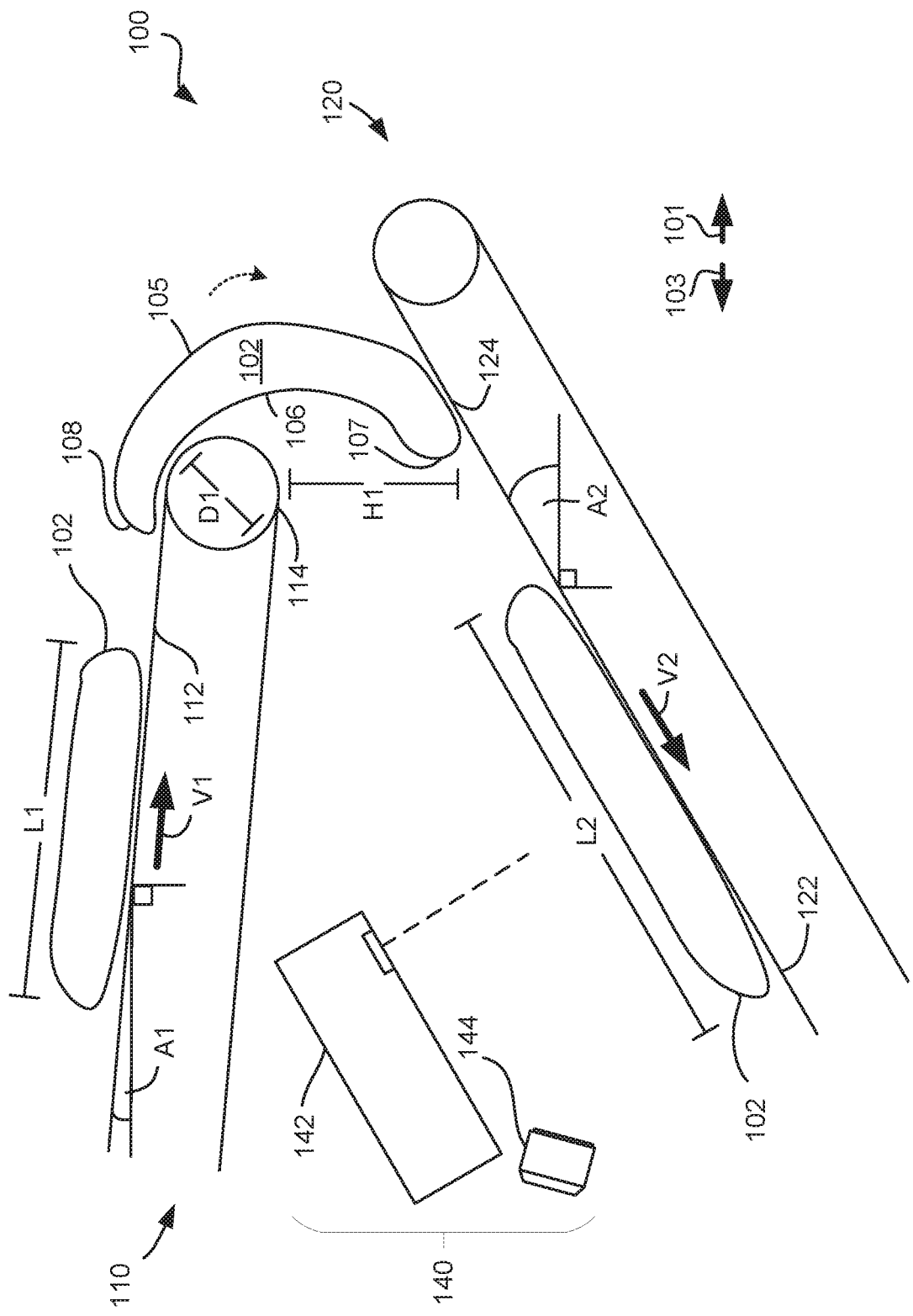
FIG. 2 depicts a close-up schematic view of a portion of the apparatus of FIG. 1, according to non-limiting examples.

FIG. 2 depicts a close-up schematic view of a portion of the apparatus 100, according to non-limiting examples. The flexible food product 102 is shown at three stages: resting on the first conveying surface 112, transferring from the first conveyor 110 to the second conveyor 120, and resting on the second conveying surface 122.

The flexible food product 102 has a first side 105, a second side 106 opposite the first side, a leading end portion 107, and a trailing end portion 108. When the flexible food product 102 is resting on the first conveying surface 112, the first side 105 of the flexible food product 102 is facing toward the upper imaging device 150 (FIG. 1), with the second side 106 resting on the first conveying surface 112. When the flexible food product 102 is resting on the second conveying surface 122, the second side 106 is facing toward the lower imaging device 140, with the first side 105 resting on the second conveying surface 122. When the flexible food product 102 is moved off the first conveyor 110, first the leading end portion 107 is moved off the terminal end 114 of the first conveyor 110, followed by the body of the flexible food product 102, followed by the trailing end portion 108. The leading end portion 107, or a portion of the body of the flexible food product 102 near thereto, may be the portion of the flexible food product 102 to first be received by the second conveyor 120 at the receiving portion 124 of the second conveyor 120.

The first conveyor 110 and second conveyor 120 are configured to flip the flexible food product 102 onto its second side 105 as it is transferred from the first conveyor 110 to the second conveyor 120. Further, the first conveyor 110 and the second conveyor 120 are configured to stretch or spread the flexible food product 102 by transfer from the first conveyor 110 to the second conveyor 120.

Flipping the flexible food product 102 is achieved, in part, by the first conveyor 110 moving the flexible food product 102 generally in a forward direction 101, and the second conveyor 120 moving the flexible food product 102 generally in a reverse direction 103, opposite to the forward direction 101. Further, configuring the first conveyor 110 and second conveyor 120 to flip the flexible food product 102 may include selecting an angle A1 of decline (e.g. from the horizontal) of the first conveying surface 112, an angle A2 of decline (e.g. from the horizontal) of the second conveying surface 122, a diameter D1 of a curvature of the terminal end 114, and a height H1 of a height between the terminal end 114 of the first conveyor 110 and the receiving portion 124 of the second conveyor 120. For example, the angle A1 of decline of the first conveying surface 112 may be between about 0 to about 30 degrees inclusive, the angle A2 of decline of the second conveying surface 122 may be between about 0 to about 60 degrees inclusive, and the height H1 [between 1 to 8 inches], the diameter D1 of a curvature of the terminal end 114 may be between about 1 to about 6 inches inclusive. These parameters may be selected such that the flexible food product 102 is flipped as it is transferred from the first conveyor 110 to the second conveyor 120, and their selection can be based on characteristics of the flexible food products and the conveyors. The selection of the angle A1, angle A2, diameter D1, and height H1 may also be made to achieve favorable stretch or spread of the flexible food product 102.

Configuring the first conveyor 110 and second conveyor 120 to stretch or spread the flexible food product 102 may include selecting a first speed V1 for the first conveyor 110 to move the flexible food product 102, and selecting a second speed V2 for the second conveyor 120 to move the flexible food product 102. In the present example, the second speed V2 is selected to be greater than the first speed V1 such that the flexible food product 102 is stretched or spread as the flexible food product 102 is transferred from the first conveyor 110 to the second conveyor 120. For example, the speed V1 for the first conveyor 110 to move the flexible food product 102 may be between about 30 to about 120 feet-per-minute (fpm), and the speed V2 for the second conveyor 120 to move the flexible food product 102 may be between about 30 to about 120 fpm. The flexible food product 102 has a first length L1 when resting on the first conveyor 110. As the flexible food product 102 is moved off the first conveyor 110, and makes contact with the second conveyor 120, the leading end portion 107 of the flexible food product 102 is thereby moved more rapidly than the trailing end portion 108 of the flexible food product 102, thereby stretching the length of the flexible food product 102. The flexible food product 102 therefore has a second length L2 when resting on the second conveyor 120, the second length L2 being greater than the first length L1. The lengths L1, L2 may be measured from the leading end portion 107 to the trailing end portion 108 of the flexible food product 102. Configuring the first conveyor 110 and second conveyor 120 to stretch or spread the flexible food product 102 may also include selecting the angle A1, angle A2, diameter D1, and height H1. In some examples, selection of these parameters may be made to achieve favorable flipping and stretching.

Thus, any folds, creases, or crevices and the like, of the flexible food product 102, may be more apparent when the flexible food product 102 is stretched to length L2 than would be apparent when the flexible food product 102 is at length L1. The imaging device 140 may thereby detect foreign material contaminating the flexible food product 102 that would otherwise have been missed under folds, inside creases or crevices, of the flexible food product 102. Further, the image data captured by the imaging device 140 may be enhanced since additional surface area may be made available for light to penetrate and interact with the matter of the flexible food product 102.

Figure 3:
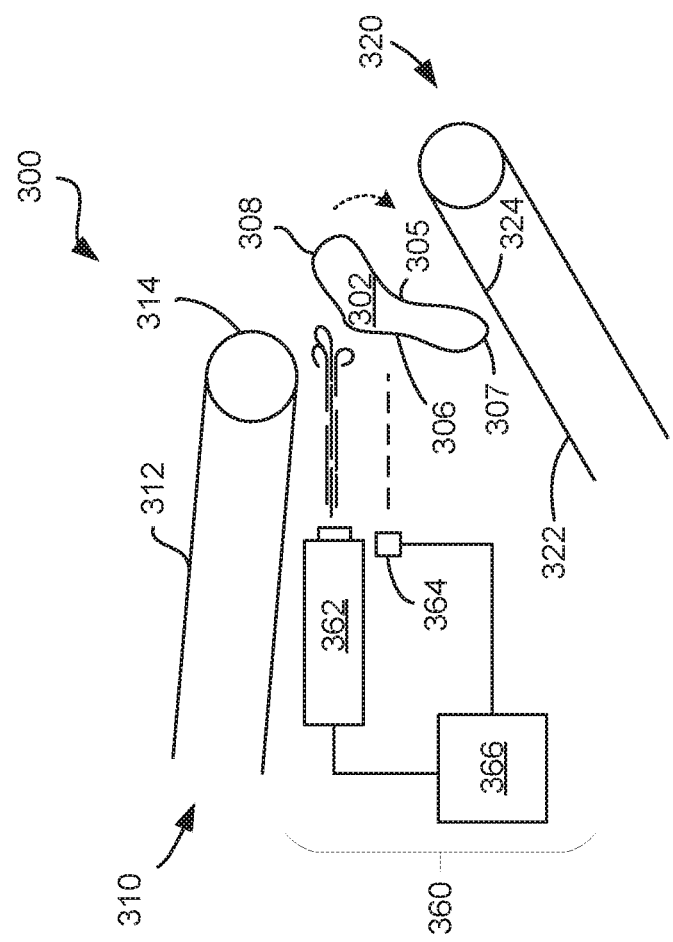
FIG. 3 depicts a close-up schematic view of a portion of another apparatus for imaging food products, the apparatus including a first guide mechanism, according to non-limiting examples.
Figure 4:
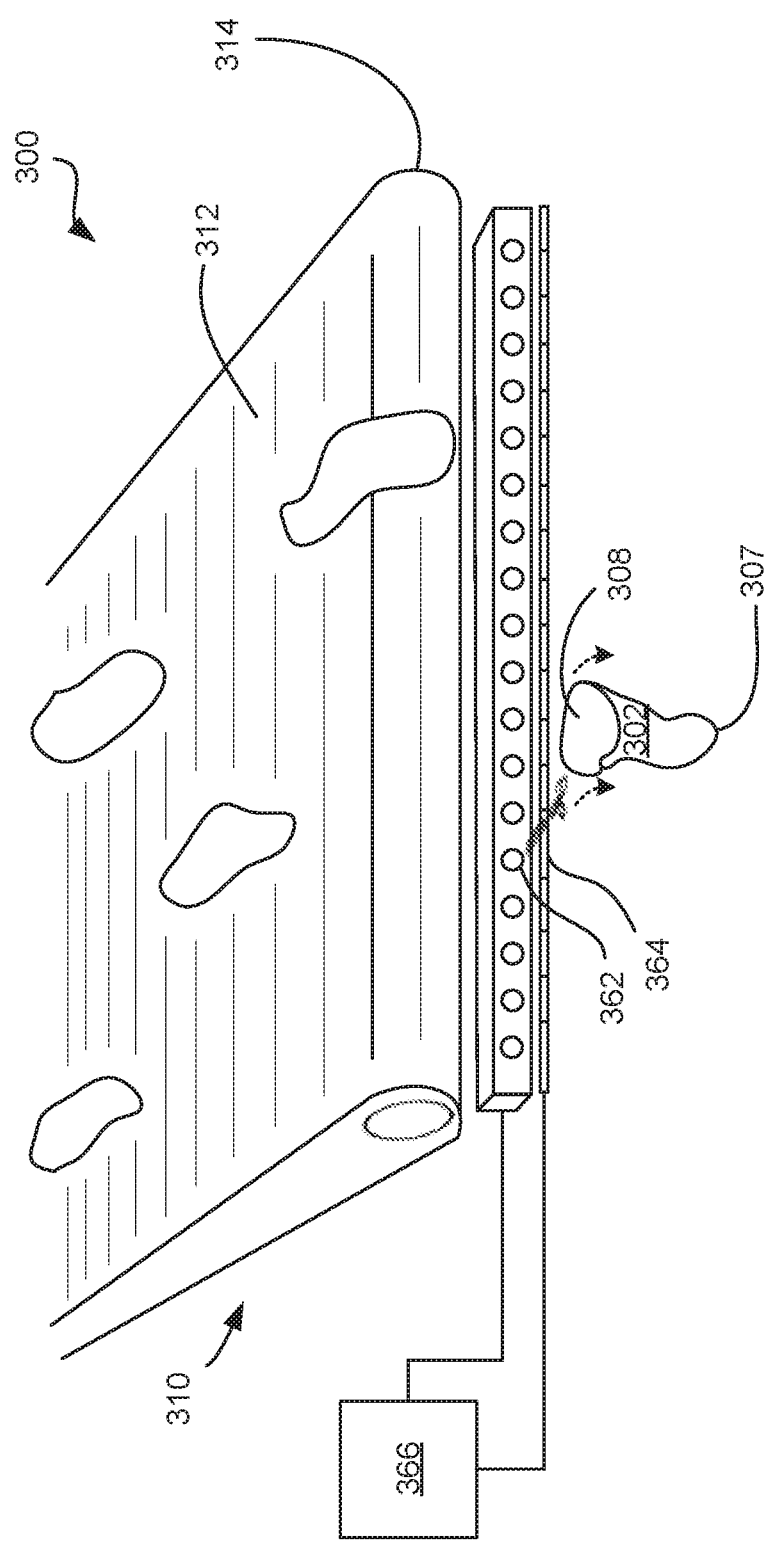
FIG. 4 depicts a schematic perspective view of the apparatus of FIG. 3, according to non-limiting examples.

FIG. 3 depicts a close-up schematic view of a portion of another apparatus 300 for imaging food products, according to non-limiting examples. FIG. 4 depicts a schematic perspective view of the apparatus 300, according to non-limiting examples. The apparatus 300 is substantially similar to the apparatus 100 with like components having like numbers, however in a "300" series rather than a "100" series.

With reference to FIG. 3 and FIG. 4, the apparatus 300 hence includes a first conveyor 310 having a first conveying surface 312 and a terminal end 314, and a second conveyor 320 having a second conveying surface 322 and a receiving portion 324. The apparatus 300 may be used to image a flexible food product 302 having a first side 305, a second side 306, a leading end portion 307, and a trailing end portion 308. For further description of the above elements of the apparatus 300, the description of the apparatus 100 of FIG. 1-2 may be referenced. For sake of clarity, only the differences between the apparatus 300 and the apparatus 100 will be described in detail. Further, an imaging device has been omitted for clarity, but the apparatus 300 is understood to include imaging devices similar to the imaging devices 140, 150.

In contrast to the apparatus 100, the apparatus 300 further includes a guide mechanism 360 to guide the flexible food product 302 to be received onto the second conveying surface 322 on its first side 305. In other words, the guide mechanism 360 is to guide the flexible food product 302 to be flipped onto its first side 305 as it is received onto the second conveying surface 322 at the receiving portion 324.

The guide mechanism 360 may include a gas deflector 362 to direct a volume of gas at the flexible food product 302. In some examples, the gas deflector 362 may be oriented to strike the trailing end portion 308 of the flexible food product with a volume of gas, thereby deflecting the trailing end portion 308 product toward the second conveying surface 322 as the flexible food product 302 moves off the terminal end 314 of the first conveyor 310. The volume of gas may strike the trailing end portion 308 on the second side 306 of the flexible food product 302.

The guide mechanism 360 may further include a position sensor 364 to take a sensor reading of a presence of the flexible food product 302 moving from the terminal end 314 of the first conveyor 310. In other words, the position sensor 364 may sense movement of the flexible food product 302 off the first conveyor 310. The position sensor 364 may be positioned above or below the gas deflector 362, or in any suitable position and orientation to detect the flexible food product 302 moving off the first conveyor 310.

The guide mechanism 360 may further include a controller 366 coupled to the position sensor and coupled to the gas deflector 362 to actuate the gas deflector 362 based on the sensor reading from the position sensor 364. The controller 366 may be programmed to receive a sensor reading from the position sensor 364, and time the actuation of gas deflector 362 such that the volume of air directed at the flexible food product 302 strikes the flexible food product 302 at a desired location, such as at the trailing end portion 308 thereof.

The gas deflector 362 may be part of a group of other gas deflectors which are oriented along a width of the first conveyor 310 (as best seen in FIG. 4). Similarly, the position sensor 364 may be part of a group of other position sensors which are oriented along a width of the first conveyor 310 (as best seen in FIG. 4). The gas deflector 362 may be configured to produce a narrow volume of gas such that an individual targeted food product may be struck with gas to flip the targeted food product without interfering with the movement of other food products which may be moving off the first conveyor 310 at the same time. Actuation of the gas deflector 362 to be timed to strike the targeted food product without interfering with the other food products. A suitable gas deflector to produce narrow volumes of gas may include an air jets or other types of gas deflectors.

Figure 5:
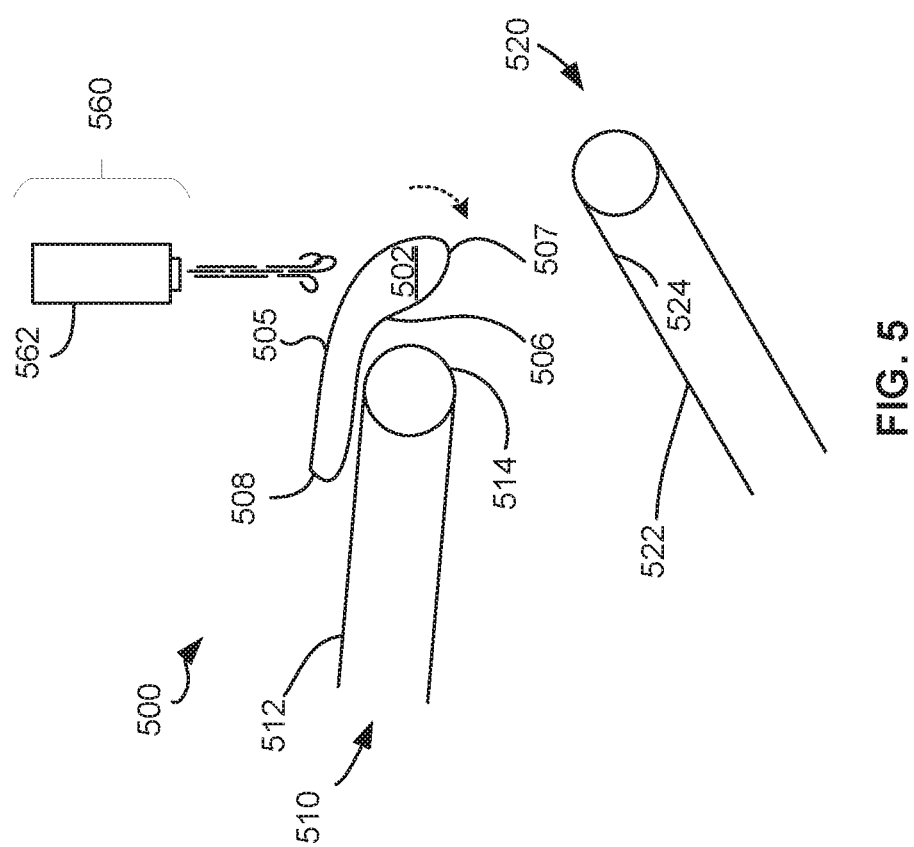
FIG. 5 depicts a close-up schematic view of a portion of another apparatus for imaging food products, the apparatus including a second guide mechanism, according to non-limiting examples.
Figure 6:
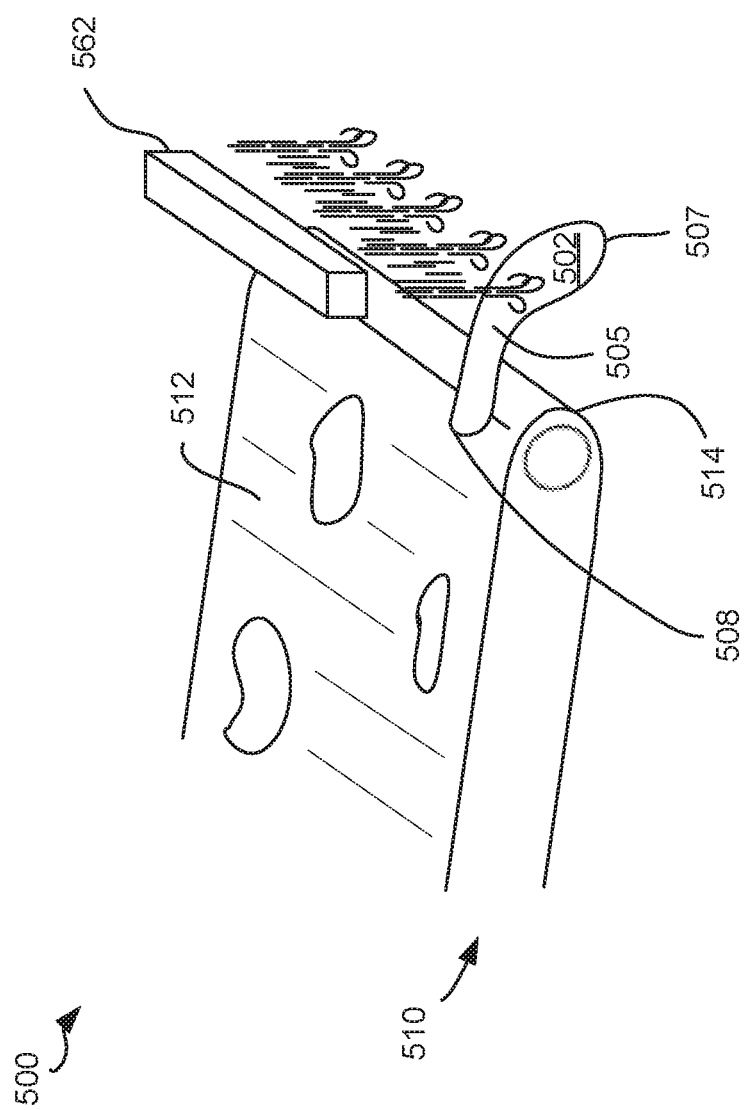
FIG. 6 depicts a schematic perspective view of the apparatus of FIG. 5, according to non-limiting examples.

FIG. 5 depicts a close-up schematic view of a portion of another apparatus 500 for imaging food products, according to non-limiting examples. FIG. 6 depicts a schematic perspective view of the apparatus 500, according to non-limiting examples. The apparatus 500 is substantially similar to the apparatus 100 with like components having like numbers, however in a "500" series rather than a "100" series.

With reference to FIG. 5 and FIG. 6, the apparatus 500 hence includes a first conveyor 510 having a first conveying surface 512 and a terminal end 514, and a second conveyor 520 having a second conveying surface 522 and a receiving portion 524. The apparatus 500 may be used to image a flexible food product 502 having a first side 505, a second side 506, a leading end portion 507, and a trailing end portion 508. For further description of the above elements of the apparatus 500, the description of the apparatus 100 of FIG. 1-2 may be referenced. For sake of clarity, only the differences between the apparatus 500 and the apparatus 100 will be described in detail. Further, an imaging device has been omitted for clarity, but the apparatus 500 is understood to include imaging devices similar to the imaging devices 140, 150.

In contrast to the apparatus 100, the apparatus 500 further includes a guide mechanism 560 to guide the flexible food product 502 to be received onto the second conveying surface 522 on its first side 505. In other words, the guide mechanism 560 is to guide the flexible food product 502 to be flipped onto its first side 505 as it is received onto the second conveying surface 522 at the receiving portion 524.

The guide mechanism 560 may include a gas deflector 562 to direct a volume of gas at the flexible food product 502. In some examples, the gas deflector 562 may be oriented to strike the leading end portion 507 of the flexible food product with a volume of gas to deflect the leading end portion 507 of the flexible food product 502 toward the second conveying surface 522 as the flexible food product 502 product moves off the terminal end 514 of the first conveyor 510. The volume of gas may strike the leading end portion 507 on the first side 505 of the flexible food product 502.

The gas deflector 562 may include an air knife or other type of gas deflector which produces a wide band of gas to be directed toward food products moving off the terminal end 514 of the first conveyor 510 (FIG. 6). A wide band of gas may provide a continuous guiding force which assists flexible food products to flip as they move off the first conveyor 510.

In some examples, the guide mechanism 560 may include a gas deflector configured to produce a narrow volume of gas to strike individual targeted food products without interfering with the movement of other food products, and may include position sensors and a controller to cooperate with the gas deflector, as discussed with reference to apparatus 300.

Figure 7:
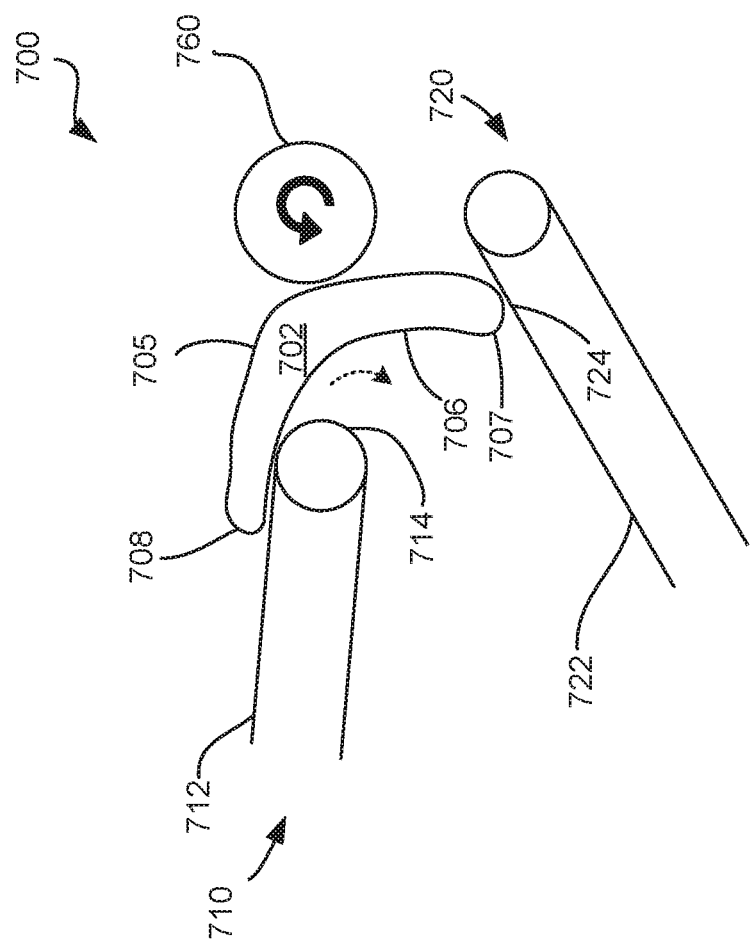
FIG. 7 depicts a close-up schematic view of a portion of another apparatus for imaging food products, the apparatus including a third guide mechanism, according to non-limiting examples.

FIG. 7 depicts a close-up schematic view of a portion of another apparatus 700 for imaging food products, according to non-limiting examples. The apparatus 700 is substantially similar to the apparatus 100 with like components having like numbers, however in a "700" series rather than a "100" series.

With reference to FIG. 7, the apparatus 700 hence includes a first conveyor 710 having a first conveying surface 712 and a terminal end 714, and a second conveyor 720 having a second conveying surface 722 and a receiving portion 724. The apparatus 700 may be used to image a flexible food product 702 having a first side 705, a second side 706, a leading end portion 707, and a trailing end portion 708. For further description of the above elements of the apparatus 700, the description of the apparatus 100 of FIG. 1-2 may be referenced. For sake of clarity, only the differences between the apparatus 700 and the apparatus 100 will be described in detail. Further, an imaging device has been omitted for clarity, but the apparatus 700 is understood to include imaging devices similar to the imaging devices 140, 150.

In contrast to the apparatus 100, the apparatus 700 may further include a roller 760 to serve as a guide mechanism to guide the flexible food product 702 to be received onto the second conveying surface 722 on its first side 705. In other words, the roller 760 is to guide the flexible food product 702 to be flipped onto its first side 705 as it is received onto the second conveying surface 722 at the receiving portion 724.

The roller 760 may be positioned to deflect the leading end portion 707 of the flexible food product 702 product toward the second conveying surface 722 as the flexible food product 702 moves off the terminal end 714 of the first conveyor 710. The roller 760 may continue to contact the flexible food product 702 at first side 705 thereof to continue to deflect the flexible food product 702. In some examples, it is contemplated that a plurality of rollers 760 may be used.

In some examples, the roller 760 may be actuated by a shaft and a motor (not shown), and the like, to turn the roller in a direction to guide the flexible food product 702 downward. In some examples, the roller 760 may be rotatably mounted on a shaft (not shown) to rotate freely.

Figure 8:
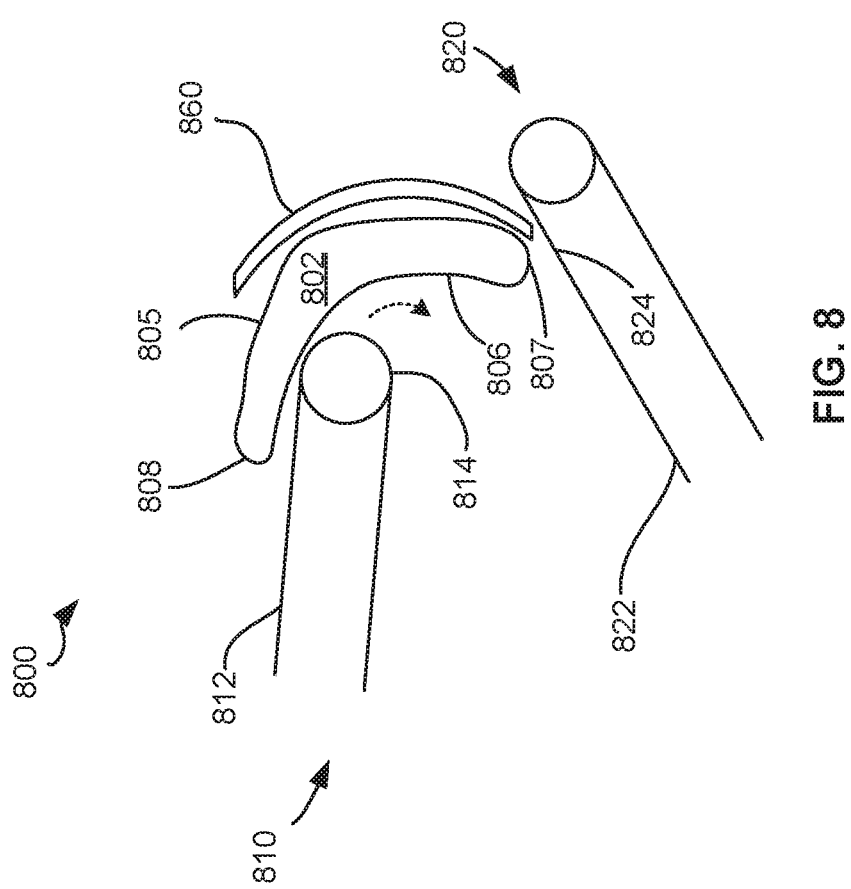
FIG. 8 depicts a close-up schematic view of a portion of another apparatus for imaging food products, the apparatus including a fourth guide mechanism, according to non-limiting examples.

FIG. 8 depicts a close-up schematic view of a portion of another apparatus 800 for imaging food products, according to non-limiting examples. The apparatus 800 is substantially similar to the apparatus 100 with like components having like numbers, however in a "800" series rather than a "100" series.

With reference to FIG. 8, the apparatus 800 hence includes a first conveyor 810 having a first conveying surface 812 and a terminal end 814, and a second conveyor 820 having a second conveying surface 822 and a receiving portion 824. The apparatus 800 may be used to image a flexible food product 802 having a first side 805, a second side 806, a leading end portion 707, and a trailing end portion 808. For further description of the above elements of the apparatus 800, the description of the apparatus 100 of FIG. 1-2 may be referenced. For sake of clarity, only the differences between the apparatus 800 and the apparatus 100 will be described in detail. Further, an imaging device has been omitted for clarity, but the apparatus 800 is understood to include imaging devices similar to the imaging devices 140, 150.

In contrast to the apparatus 100, the apparatus 800 further includes a deflecting sheet 860 to serve as a guide mechanism to guide the flexible food product 802 to be received onto the second conveying surface 822 on its first side 805. In other words, the deflecting sheet 860 is to guide the flexible food product 802 to be flipped onto its first side 805 as it is received onto the second conveying surface 822 at the receiving portion 824. In some examples, the deflecting sheet 860 may be curved. For example, the deflecting sheet 860 may be curved concave inward toward the direction of the terminal end 814 of the first conveyor 810.

The deflecting sheet 860 may be positioned to deflect the leading end portion 807 of the flexible food product 802 product toward the second conveying surface 822 as the flexible food product 802 moves off the terminal end 814 of the first conveyor 810. The deflecting sheet 860 may continue to contact the flexible food product 802 at first side 805 thereof to continue to deflect the flexible food product 802. In some examples, it is contemplated that a plurality of deflecting sheets 860 may be used.

Figure 9:
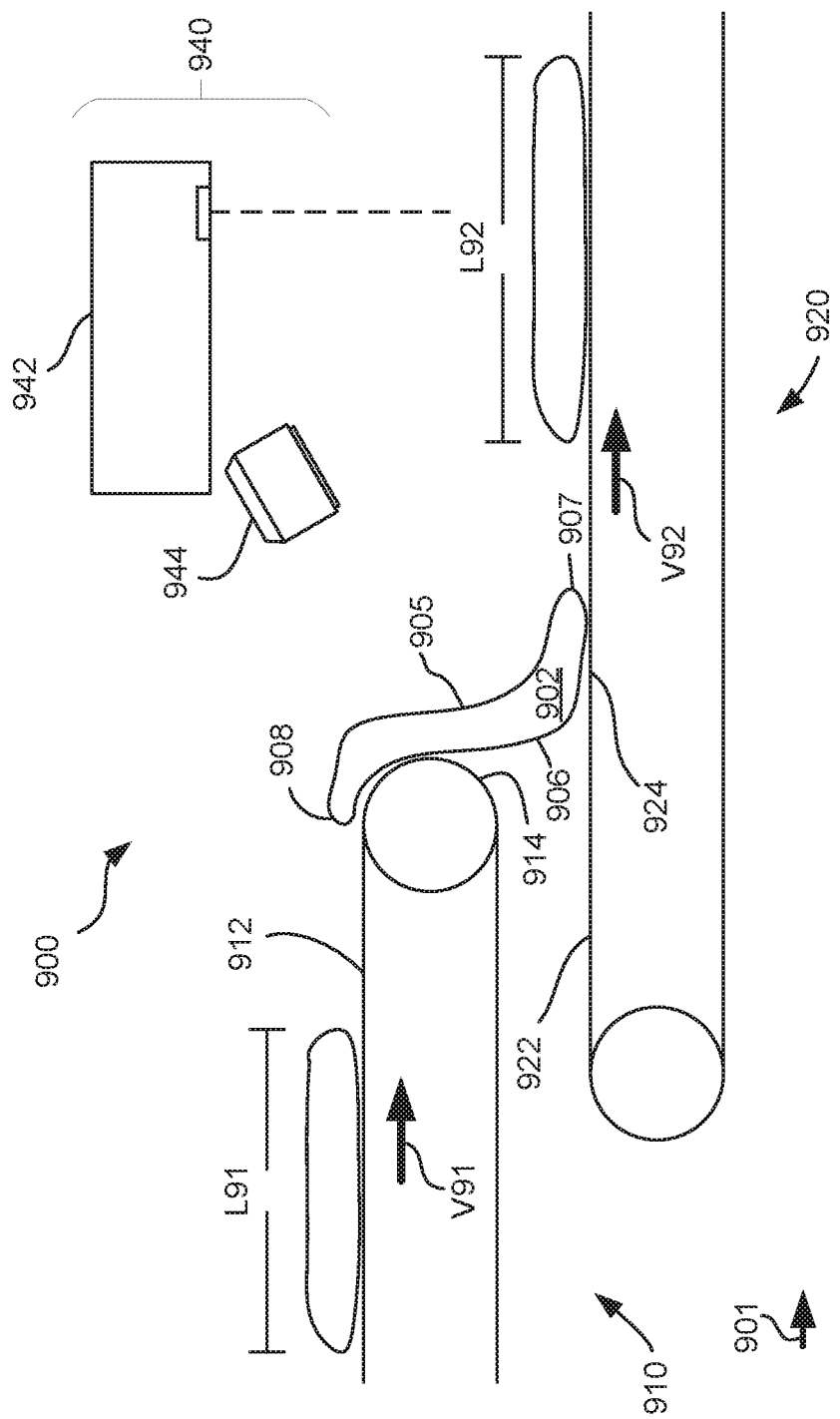
FIG. 9 depicts a schematic view of another apparatus for imaging food products with conveyors configured in a tumble waterfall configuration, according to non-limiting examples.

FIG. 9 depicts a schematic view of another apparatus 900 for imaging food products, according to non-limiting examples. The apparatus 900 is substantially similar to the apparatus 100 with like components having like numbers, however in a "900" series rather than a "100" series.

With reference to FIG. 9, the apparatus 900 hence includes a first conveyor 910 having a first conveying surface 912 and a terminal end 914, a second conveyor 920 having a second conveying surface 922 and a receiving portion 924, and an imaging device 940 including an imager 942 and a lighting device 944. The apparatus 900 may be used to image a flexible food product 902 having a first side 905, a second side 906, a leading end portion 907, and a trailing end portion 908. For further description of the above elements of the apparatus 900, the description of the apparatus 100 of FIG. 1-2 may be referenced. For sake of clarity, only the differences between the apparatus 900 and the apparatus 100 will be described in detail.

In contrast to the apparatus 100, the first conveyor 910 and second conveyor 920 are configured in a tumble waterfall configuration. In a tumble waterfall configuration, the receiving portion 924 of the second conveyor 920 is positioned in a downward direction from the terminal end 914 of the first conveyor 910, and the first conveyor 910 and second conveyor 920 both move the flexible food product 902 in the forward direction 901.

As with the apparatus 100, the first conveyor 910 may move the flexible food product 902 at a first speed V91 and the second conveyor 920 may move the flexible food product 902 at a second speed V92, where the second speed V92 is selected to be greater than the first speed V91 such that the flexible food product 902 is stretched or spread as the flexible food product 902 is transferred from the first conveyor 910 to the second conveyor 920. The flexible food product 902 may therefore have a first length L91 when resting on the first conveyor 910, and a second length L92 when resting on the second conveyor 920, which is lengthened by stretching or spreading of the flexible food product 902 as the flexible food product 902 is moved off the first conveyor 910.

Further, in contrast to the apparatus 100, the first side 905 of the flexible food product 902 may face upward while resting on both the first conveying surface 912 and the second conveying surface 922. Thus, the flexible food product 102 may not be flipped during transfer from the first conveyor 910 to the second conveyor 920. Thus, the imaging device 940 may capture an image of the flexible food product 902 as viewed from its first side 905.

However, although the first conveyor 910 and second conveyor 920 are both shown to move the flexible food product 902 in the forward direction 901, it is contemplated that, in some examples, the second conveyor 920 may move the flexible food product 902 in a reverse direction opposite to the forward direction 901, thereby flipping the flexible food product 902.

Further, it is contemplated that, in some examples, the apparatus 900 may further include an imaging device oriented to capture an image of the flexible food product 902 on the first conveyor 910. Thus, images of the flexible food product 902 may be captured before and after transfer from the first conveyor 910 to the second conveyor 920.

Figure 10:
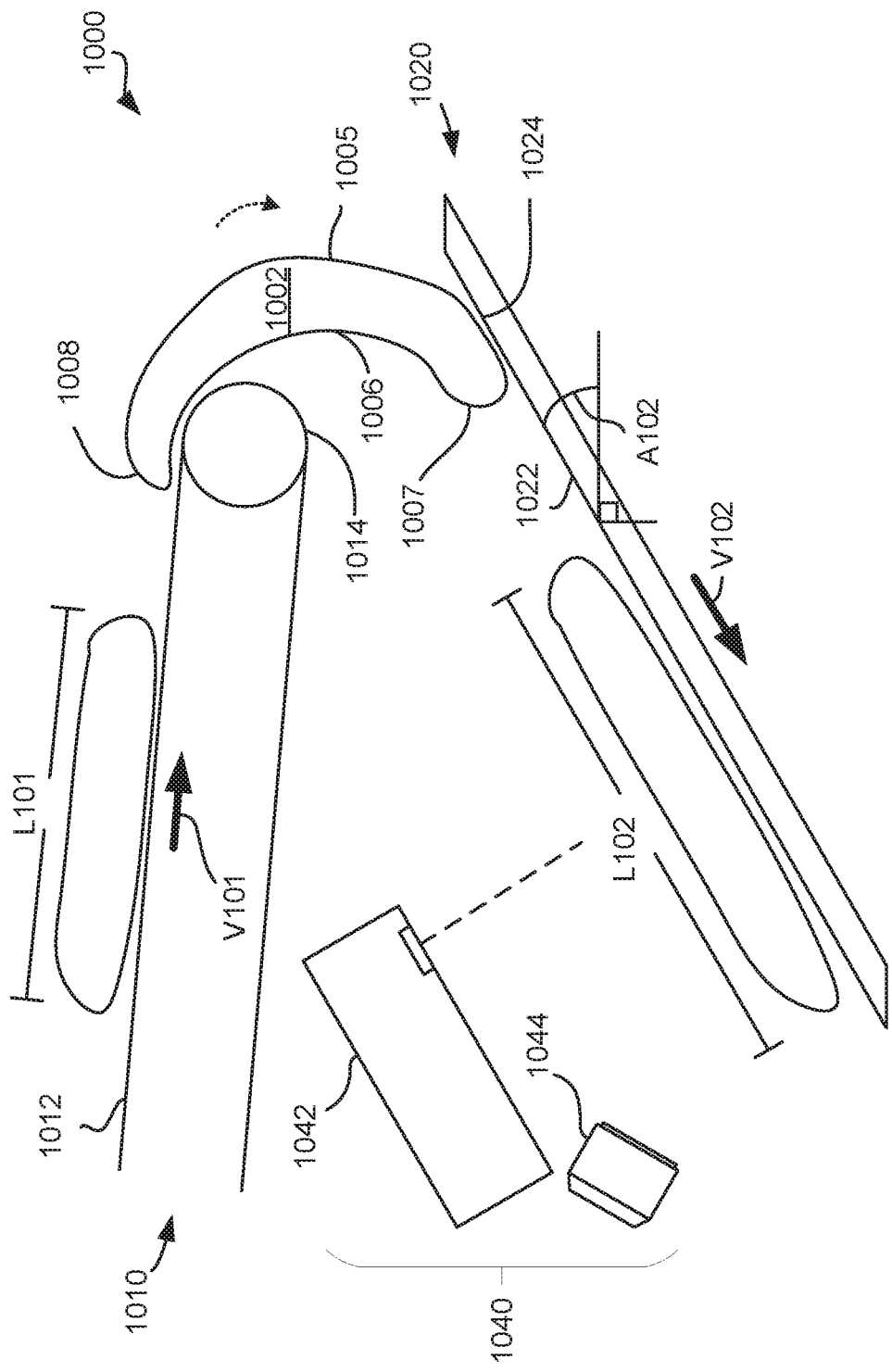
FIG. 10 depicts a close up schematic view of another apparatus for imaging food products, the apparatus including a receiving structure having a low-friction receiving surface, according to non-limiting examples.

FIG. 10 depicts a close up schematic view of another apparatus 1000 for imaging food products, according to non-limiting examples. The apparatus 1000 is substantially similar to the apparatus 100 with like components having like numbers, however in a "1000" series rather than a "100" series.

With reference to FIG. 10, the apparatus 1000 hence includes a first conveyor 1010 having a first conveying surface 1012 and a terminal end 1014, and an imaging device 1040 including an imager 1042 and a lighting device 1044. The apparatus 1000 may be used to image a flexible food product 1002 having a first side 1005, a second side 1006, a leading end portion 1007, and a trailing end portion 1008. For further description of the above elements of the apparatus 1000, the description of the apparatus 100 of FIG. 1-2 may be referenced. For sake of clarity, only the differences between the apparatus 1000 and the apparatus 100 will be described in detail.

In contrast to the apparatus 100, the apparatus 1000 further includes a receiving structure 1020, such as a slide or a chute, having a receiving surface 1022 oriented at an angle A102 of decline and a receiving portion 1024. The receiving surface 1022 may include a low-friction surface which allows the flexible food product 1002 to travel more quickly down the receiving surface 1022 at a speed V102 that is greater than the speed V101 at which the flexible food product 1002 is moved by the first conveyor 1010. The angle A102 and the friction of the receiving surface 1022 may be selected to adjust the speed V102 at which the flexible food product 1002 is moved down the receiving surface 1022. Thus, that the flexible food product 1002 may be stretched or spread from a first length L101 to a second length L102 as the flexible food product 1002 is transferred from the first conveyor 1010 to the receiving structure 1020. As the flexible food product 1002 is moved off the first conveyor 1010, and makes contact with the receiving structure 1020, the leading end portion 1007 of the flexible food product 1002 is thereby moved more rapidly than the trailing end portion 1008, thereby stretching the length of the flexible food product 1002.

It is further contemplated, that in some examples, the apparatus 1000 may include a first receiving structure (e.g. a first slide or chute, not shown) and a second receiving structure (e.g. receiving structure 1020), where both receiving surfaces are oriented at angles of decline, and wherein a flexible food product 1002 may travel more quickly down the second receiving structure than the first receiving structure to stretch the flexible food product 1002.

Further, it is contemplated that, in some examples, the apparatus 1000 may further include an imaging device oriented to capture an image of the flexible food product 1002 on the first conveyor 1010. Thus, images of the flexible food product 1002 may be captured before and after transfer from the first conveyor 1010 to the second conveyor 1020.

Figure 11:
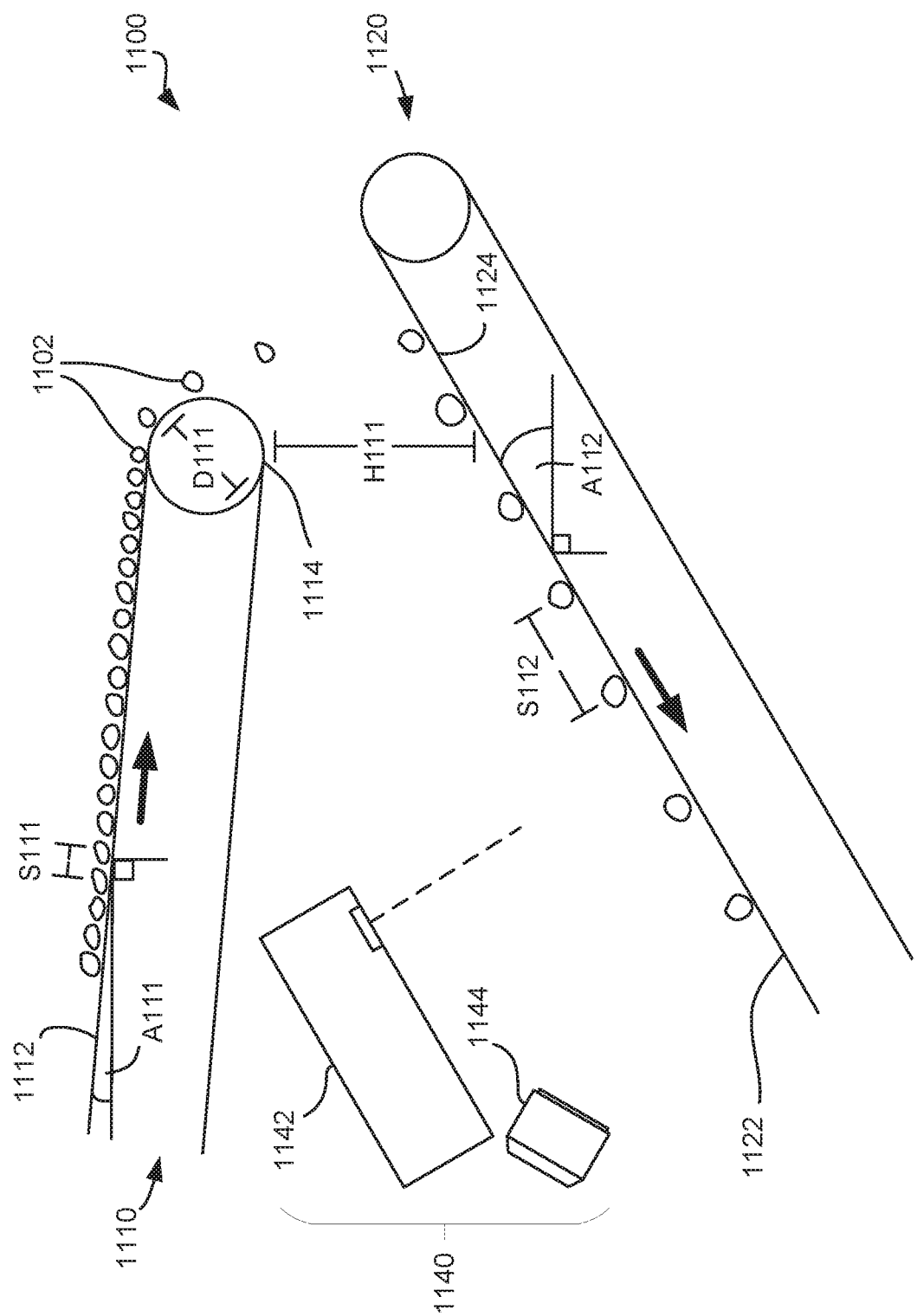
FIG. 11 depicts a close up schematic view of another apparatus for imaging food products, according to non-limiting examples.

FIG. 11 depicts a schematic view of another apparatus 1100 for imaging food products, according to non-limiting examples. The apparatus 1100 is substantially similar to the apparatus 100 with like components having like numbers, however in a "1100" series rather than a "100" series.

With reference to FIG. 11, the apparatus 1100 hence includes a first conveyor 1110 having a first conveying surface 1112 and a terminal end 1114, a second conveyor 1120 having a second conveying surface 1122 and a receiving portion 1124, and an imaging device 1140 including an imager 1142 and a lighting device 1144. For further description of the above elements of the apparatus 1100, the description of the apparatus 100 of FIG. 1-2 may be referenced. For sake of clarity, only the differences between the apparatus 1100 and the apparatus 100 will be described in detail.

The apparatus 1100 may be used to image a plurality of food products 1102. The food products 1102 may be densely spaced apart by a first spacing distance S111 when resting on the first conveyor 1110. At the first spacing distance S111, the food products 1102 may bunch up, overlap, or otherwise obscure each other from view.

The first conveyor 1110 may move the food products 1102 at a first speed V111 and the second conveyor 1120 may move the food products 1102 at a second speed V112, where the second speed V112 is selected to be greater than the first speed V111 such that the food products 1102 are further spread or spaced apart on the second conveyor 1120, by a second spacing distance S112, which is greater than the first spacing distance S111. Thus, bunches and dense groups of the food products 1102 may be spread apart such that the food products 1102 may be analyzed.

Further, configuring the first conveyor 1110 and second conveyor 1120 to spread apart the food products 1102 may include selecting an angle A111 of decline of the first conveying surface 1112, an angle A112 of decline of the second conveying surface 1122, a diameter D111 of a curvature of the terminal end 1114, and a height H111 of a height between the terminal end 1114 of the first conveyor 1110 and the receiving portion 1124 of the second conveyor 1120.

It is also contemplated that, in some examples, a receiving having a low-friction receiving surface structure may be used to receive the food products 1102, whereby movement of the food products 1102 on the low-friction receiving surface is faster than the movement of the food products 1102 on the first conveyor 1110, thereby spreading or spacing apart the food products 1102.

It is further contemplated that, in some examples, the apparatus 1100 may include guides to group the food products 1102 into laneways on the conveyor 1110 and/or conveyor 1120. The guides may further separate the food products 1102 with respect to the width of the conveyors 1110, 1120, which may reduce viewing obstruction of the food products 1102, and which may further facilitate separation and/or removal of groups of food products 1102.

Further, it is contemplated that, in some examples, the apparatus 1100 may further include an imaging device oriented to capture an image of the food products 1102 on the first conveyor 1110. Thus, images of the food products 1102 may be captured before and after transfer from the first conveyor 1110 to the second conveyor 1120.

In addition to spreading apart the food products 1102, transference from the first conveyor 1110 to the second conveyor 1120 may also flip or rotate a portion of the food products 1102. Thus, images of first sides of some of the food products 1102 may be captured on the first conveyor 1110, and images of second sides of food products 1102 which have been flipped or rotated may be captured on the second conveyor 1120. Thus, images of different sides of the food products 1102 may be captured.

Figure 12:
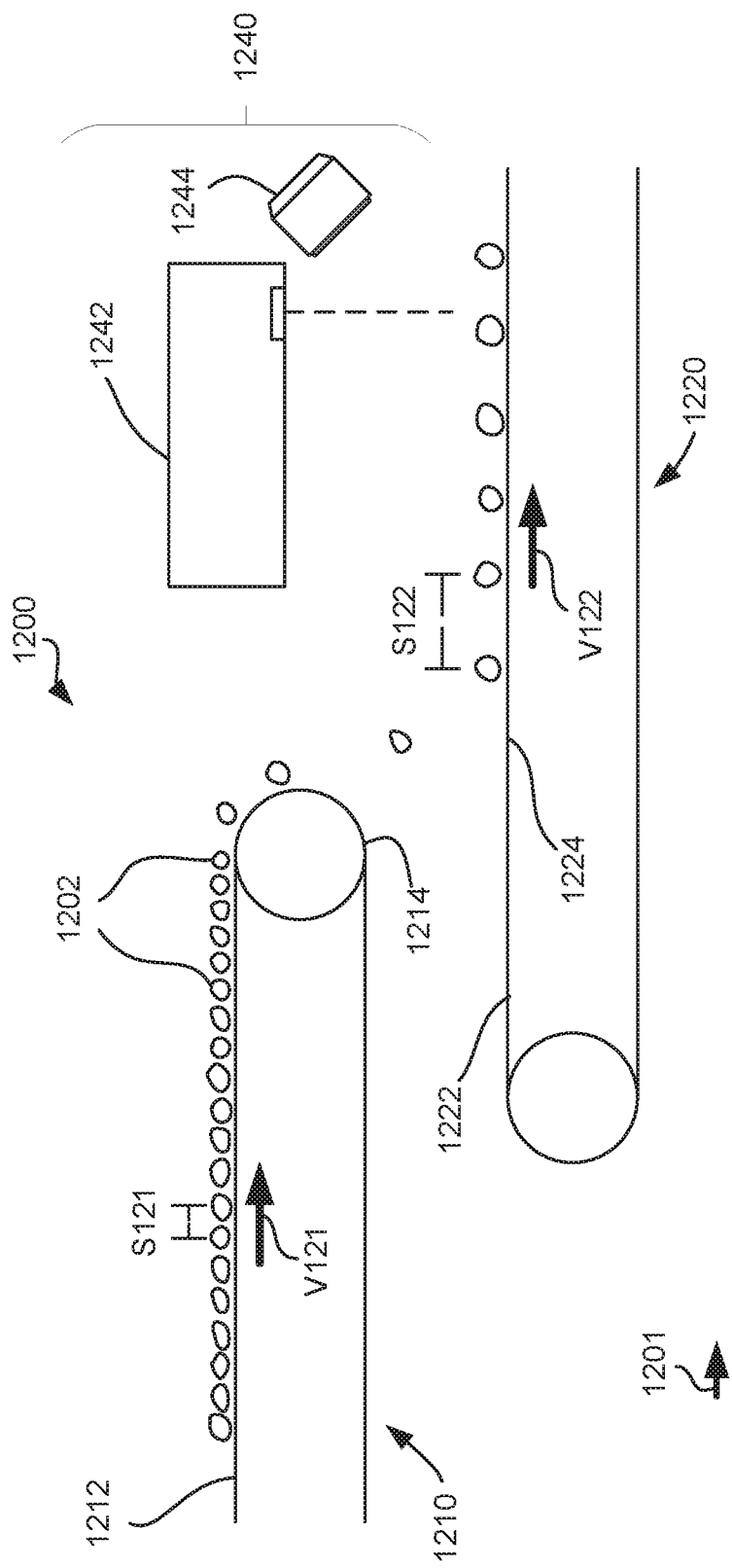
FIG. 12 depicts a schematic view of another apparatus for imaging food products with conveyors configured in a tumble waterfall configuration, according to non-limiting examples.

FIG. 12 depicts a schematic view of another apparatus 1200 for imaging food products. The apparatus 1200 is substantially similar to the apparatus 1100 with like components having like numbers, however in a "1200" series rather than a "1100" series.

With reference to FIG. 12, the apparatus 1200 hence includes a first conveyor 1210 having a first conveying surface 1212 and a terminal end 1214, a second conveyor 1220 having a second conveying surface 1222 and a receiving portion 1224, and an imaging device 1240 including an imager 1242 and a lighting device 1244. For further description of the above elements of the apparatus 1200, the description of the apparatus 1100 of FIG. 11 may be referenced. For sake of clarity, only the differences between the apparatus 1200 and the apparatus 1100 will be described in detail.

The first conveyor 1210 and second conveyor 1220 may be configured in a tumble waterfall configuration. In a tumble waterfall configuration, the receiving portion 1224 of the second conveyor 1220 is positioned in a downward direction from the terminal end 1214 of the first conveyor 1210, and the first conveyor 1210 and second conveyor 1220 both move flexible food products in the forward direction 1201.

The apparatus 1200 may be used to image a plurality of food products 1202. The food products 1202 may be densely spaced apart by a first spacing distance S121 when resting on the first conveyor 1210. At the first spacing distance S121, the food products 1202 may bunch up, overlap, or otherwise obscure each other from view.

The first conveyor 1210 may move the food products 1202 at a first speed V121 and the second conveyor 1220 may move the food products 1202 at a second speed V122, where the second speed V122 is selected to be greater than the first speed V121 such that the food products 1202 are further spread or spaced apart on the second conveyor 1220, by a second spacing distance S122, which is greater than the first spacing distance S121. Thus, bunches and dense groups of the food products 1202 may be spread apart such that the food products 1202 may be analyzed.

It is further contemplated that, in some examples, the apparatus 1200 may include guides to group the food products 1202 into laneways on the conveyor 1210 and/or conveyor 1220. The guides may further separate the food products 1202 with respect to the width of the conveyors 1210, 1220, which may reduce viewing obstruction of the food products 1202, and which may further facilitate separation and/or removal of groups of food products 1202.

Further, it is contemplated that, in some examples, the apparatus 1200 may further include an imaging device oriented to capture an image of the food products 1202 on the first conveyor 1210. Thus, images of the food products 1202 may be captured before and after transfer from the first conveyor 1210 to the second conveyor 1220.

In addition to spreading apart the food products 1202, transference from the first conveyor 1210 to the second conveyor 1220 may also flip or rotate a portion of the food products 1202. Thus, images of first sides of some of the food products 1202 may be captured on the first conveyor 1210, and images of second sides of food products 1202 which have been flipped or rotated may be captured on the second conveyor 1220. Thus, images of different sides of the food products 1202 may be captured.

Thus, it can be seen that apparatuses for imaging food products may be provided which include conveyors which flip, stretch, spread, spread apart, or otherwise manipulate food products for imaging. An apparatus includes a first conveyor and a second conveyor below the first conveyor, with the first conveyor to move foods products at a greater speed than the second conveyor to stretch flexible food products. The conveyors are configured to flip the food products as they are stretched. The apparatus includes an imaging device to image the flexible food products after being stretched.

Another apparatus includes a first conveyor and a second conveyor below the first conveyor, with the first conveyor to move foods products at a greater speed than the second conveyor to stretch flexible food products. The conveyors are configured to flip the flexible food products as they are stretched. The apparatus includes a first imaging device to image the flexible food products before being stretched and a second imaging device to image the flexible food products after being stretched. The apparatus includes a guide mechanism to guide the food product to be flipped.

Another apparatus includes a first conveyor and a second conveyor below the first conveyor, with the first conveyor to move a plurality of foods products at a greater speed than the second conveyor to spread apart the food products. The apparatus includes an imaging device to image the food products after being spread apart.

Another apparatus includes a conveyor and a receiving structure below the conveyor, with the receiving structure having a low-friction receiving surface to move a food product at a greater speed along the receiving structure than along the first conveyor, thereby stretching, spreading, or spreading apart the food product.

Another apparatus may include a guide mechanism such an air jet, air knife, roller, or deflecting sheet, to assist with flipping food products. In some examples, the apparatus may include a first conveyor and a second conveyor, wherein the second conveyor moves the food products at a speed greater than or equal to the speed at which the first conveyor moves the food products (e.g. including where the second conveyor moves the food products at the same speed as the first conveyor), wherein a guide mechanism guides the transfer of the food products from the first conveyor to the second conveyor.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" can be construed as X only, Y only, Z only, or any combination of two or more items X, Y, and Z (e.g., XYZ, XY, YZ, XZ, and the like). Similar logic can be applied for two or more items in any occurrence of "at least one . . . " and "one or more . . . " language.

The terms "about", "substantially", "essentially", "approximately", and the like, are defined as being "close to", for example as understood by persons of skill in the art. In some embodiments, the terms are understood to be "within 10%," in other embodiments, "within 5%", in yet further embodiments, "within 1%", and in yet further embodiments "within 0.5%".

Persons skilled in the art will appreciate that in some embodiments, the functionality of devices and/or methods and/or processes described herein can be implemented using pre-programmed hardware or firmware elements (e.g., application specific integrated circuits (ASICs), electrically erasable programmable read-only memories (EEPROMs), etc.), or other related components. In other embodiments, the functionality of the devices and/or methods and/or processes described herein can be achieved using a computing apparatus that has access to a code memory (not shown) which stores computer-readable program code for operation of the computing apparatus. The computer-readable program code could be stored on a computer readable storage medium which is fixed, tangible and readable directly by these components, (e.g., removable diskette, CD-ROM, ROM, fixed disk, USB drive). Furthermore, it is appreciated that the computer-readable program can be stored as a computer program product comprising a computer usable medium. Further, a persistent storage device can comprise the computer readable program code. It is yet further appreciated that the computer-readable program code and/or computer usable medium can comprise a non-transitory computer-readable program code and/or non-transitory computer usable medium. Alternatively, the computer-readable program code could be stored remotely but transmittable to these components via a modem or other interface device connected to a network (including, without limitation, the Internet) over a transmission medium. The transmission medium can be either a non-mobile medium (e.g., optical and/or digital and/or analog communications lines) or a mobile medium (e.g., microwave, infrared, free-space optical or other transmission schemes) or a combination thereof.

Persons skilled in the art will appreciate that there are yet more alternative embodiments and modifications possible, and that the above examples are only illustrations of one or more embodiments. The scope, therefore, is only to be limited by the claims appended hereto.

What is claimed is:

1. An apparatus for imaging flexible food products, the apparatus comprising:
   a first conveyor having a first conveying surface and a terminal end, the first conveyor configured to move a flexible food product at a first speed on the first conveying surface off the terminal end of the first conveyor;
   a second conveyor having a second conveying surface and a receiving portion, the second conveying surface at the receiving portion positioned in a downward direction relative to the terminal end of the first conveyor to receive the flexible food product moved off the terminal end of the first conveyor, thereby flipping the flexible food product, the second conveyor configured to move the flexible food product at a second speed greater than the first speed to stretch the flexible food product as it is received by the second conveying surface;
   an upper line-scan spectrometer oriented to capture a first image of the flexible food product on the first conveying surface prior to being flipped; and
   a lower line-scan spectrometer oriented to capture a second image of the flexible food product on the second conveying surface after being flipped and stretched to reveal one or more of folds, creases, and crevices that obscure portions of the flexible food product from a view of the upper line-scan spectrometer, such that the lower line-scan spectrometer is able detect any foreign material contaminating the flexible food product that would otherwise have been obscured from view.

2. The apparatus of claim 1, wherein the flexible food product comprises a first side and a second side opposite the first side, the second side facing the lower line-scan spectrometer when the flexible food product is on the second conveying surface, and wherein the apparatus further comprises a guide mechanism to guide the flexible food product to be received onto the second conveying surface on its first side.

3. The apparatus of claim 2, wherein the guide mechanism comprises a gas deflector configured to direct a volume of gas at the flexible food product.

4. The apparatus of claim 3, wherein the gas deflector is oriented to strike a leading end portion of the flexible food product with a volume of gas to deflect the leading end portion of the flexible food product toward the second conveying surface as the flexible food product moves off the terminal end of the first conveyor.

5. The apparatus of claim 4, wherein the gas deflector comprises an air knife.

6. The apparatus of claim 3, wherein the gas deflector is oriented to strike a trailing end portion of the flexible food product with a volume of gas to deflect the trailing end portion of the flexible food product toward the second conveying surface as the flexible food product moves off the terminal end of the first conveyor.

7. The apparatus of claim 6, wherein:
   the apparatus further comprises a plurality of air jets, the gas deflector being a first air jet of the plurality of air jets;
   the apparatus further comprises a position sensor to take a sensor reading of a presence of the flexible food product moving from the terminal end of the first conveyor; and
   the apparatus further comprises a controller coupled to the position sensor and coupled to the plurality of air jets, the controller to actuate the gas deflector based on the sensor reading.

8. The apparatus of claim 1, wherein the first conveying surface is oriented at a first angle of decline, the second conveying surface is oriented at a second angle of decline.

9. An apparatus for imaging food products, the apparatus comprising:
   a first conveyor having a first conveying surface and a terminal end, the first conveyor configured to move a food product at a first speed on the first conveying surface off the terminal end, the food product comprising a first side and a second side opposite the first side, the first side facing away from the first conveying surface when the food product is on the first conveying surface;
   a second conveyor having a second conveying surface and a receiving portion, the second conveying surface at the receiving portion positioned in a downward direction relative to the terminal end of the first conveyor to receive the food product moved off the terminal end of the first conveyor;
   a guide mechanism to guide the food product to be flipped onto its first side to be received onto the second conveying surface;
   an upper line-scan spectrometer oriented to capture a first image of the food product on the first conveying surface prior to being flipped;
   a lower line-scan spectrometer oriented to capture a second image of the food product on the second conveying surface after being flipped.

10. The apparatus of claim 9, wherein the guide mechanism comprises a gas deflector configured to direct a volume of gas at the food product.

11. The apparatus of claim 10, wherein the gas deflector is oriented to strike a leading end portion of the food product with a volume of gas to deflect the leading end portion of the food product toward the second conveying surface as the food product moves off the terminal end of the first conveyor.

12. The apparatus of claim 11, wherein the gas deflector comprises an air knife.

13. The apparatus of claim 10, wherein the gas deflector is oriented to strike a trailing end portion of the food product with a volume of gas to deflect the trailing end portion of the food product toward the second conveying surface as the food product moves off the terminal end of the first conveyor.

14. The apparatus of claim 13, wherein:
the apparatus further comprises a plurality of air jets, the gas deflector being a first air jet of the plurality of air jets;
the apparatus further comprises a position sensor to take a sensor reading of a presence of the food product moving from the terminal end of the first conveyor; and
the apparatus further comprises a controller coupled to the position sensor and coupled to the plurality of air jets, the controller to actuate the gas deflector based on the sensor reading.

15. The apparatus of claim 9, wherein the guide mechanism comprises a roller positioned to deflect a leading end portion of the food product toward the second conveying surface as the food product moves off the terminal end of the first conveyor.

16. The apparatus of claim 9, wherein the guide mechanism comprises a deflecting sheet.

17. An apparatus for imaging food products, the apparatus comprising:
a first conveyor having a first conveying surface and a terminal end, the first conveyor configured to move a plurality of food products at a first speed on the first conveying surface off the terminal end;
a second conveyor having a second conveying surface to receive the plurality of food products moved off the terminal end of the first conveyor, the second conveyor configured to move the plurality of food products at a second speed greater than the first speed to one or more of flip, rotate and spread apart the plurality of food products;
an upper line-scan spectrometer oriented to capture a first image of the plurality of food products on the first conveying surface prior to the plurality of food products being one or more of flipped, rotated and spread apart; and
a lower line-scan spectrometer oriented to capture a second image of the plurality of food products on the second conveying surface after the plurality of food products are one or more of flipped, rotated and spread apart, such that the lower line-scan spectrometer images the plurality of food products with reduced obstruction therebetween to facilitate one or more of separation and removal of groups of the plurality of the food products.

\* \* \* \* \*